(12) United States Patent
Ionasec et al.

(10) Patent No.: US 11,393,576 B2
(45) Date of Patent: Jul. 19, 2022

(54) METHOD FOR SETTING A MEDICAL IMAGING PROTOCOL, SYSTEM FOR SETTING A MEDICAL INSTRUMENT, COMPUTER PROGRAM AND COMPUTER-READABLE MEDIUM

(71) Applicant: Siemens Healthcare GmbH, Erlangen (DE)

(72) Inventors: Razvan Ionasec, Nuremberg (DE); Philipp Hoelzer, Baltimore, MD (US)

(73) Assignee: Siemens Healthcare GmbH, Erlangen (DE)

( * ) Notice: Subject to any disclaimer, the term of this patent is extended or adjusted under 35 U.S.C. 154(b) by 77 days.

(21) Appl. No.: 16/753,195

(22) PCT Filed: Sep. 26, 2018

(86) PCT No.: PCT/EP2018/076149
§ 371 (c)(1),
(2) Date: Apr. 2, 2020

(87) PCT Pub. No.: WO2019/068536
PCT Pub. Date: Apr. 11, 2019

(65) Prior Publication Data
US 2020/0335201 A1    Oct. 22, 2020

(30) Foreign Application Priority Data
Oct. 5, 2017 (EP) .................................... 17194984

(51) Int. Cl.
*G16H 30/00* (2018.01)
*G16H 30/40* (2018.01)
(Continued)

(52) U.S. Cl.
CPC .............. *G16H 30/40* (2018.01); *G06N 7/005* (2013.01); *G16H 40/63* (2018.01); *G16H 50/20* (2018.01)

(58) Field of Classification Search
CPC ........ G16H 30/40; G16H 50/20; G16H 40/63; G06N 7/005
See application file for complete search history.

(56) References Cited

U.S. PATENT DOCUMENTS

| 2006/0200010 A1* | 9/2006 | Rosales .................. G16H 50/70 128/920 |
| 2009/0006131 A1* | 1/2009 | Unger ..................... G16H 50/20 705/3 |
| 2018/0011980 A1 | 1/2018 | Contu et al. |

FOREIGN PATENT DOCUMENTS

WO    WO 2016097886 A1    6/2016

OTHER PUBLICATIONS

European Summons to attend oral proceedings dated May 17, 2021.
(Continued)

*Primary Examiner* — Khai M Nguyen
(74) *Attorney, Agent, or Firm* — Harness, Dickey & Pierce, P.L.C.

(57) ABSTRACT

A method for setting a medical imaging protocol includes providing an information data set assigned to a patient. The information data set includes an information about a provisional diagnostic finding regarding the patient. In an embodiment, the method further includes assigning a probability value for a positive finding of the provisional diagnostic finding to the information data set; and automatically setting the medical imaging protocol. The medical imaging protocol is adapted to the provisional diagnostic finding such that an analysis of a result of the medical imaging protocol changes the probability value.

20 Claims, 2 Drawing Sheets

(51) Int. Cl.
*G16H 50/20* (2018.01)
*G16H 40/63* (2018.01)
*G06N 7/00* (2006.01)

(56) References Cited

OTHER PUBLICATIONS

Hegedus Eric J. et al.: "Beyond SpPIN and SnNOUT: Considerations with Dichotomous Tests During Assessment of Diagnostic Accuracy", Clnimetrics Corner, The Journal of Manual & Manipulative Therapy, vol. 17, No. 1, Jan. 2009.
International Search Report PCT/ISA/210 for International Application No. PCT/EP2018/076149 dated Jan. 22, 2019.
Extended European Search Report for European Application No. 17194984.5 dated Mar. 28, 2018.
European Office Action for European Application No. 17194984.5 dated Mar. 27, 2020.
Written Opinion of the International Searching Authority PCT/ISA/237 for International Application No. PCT/EP2018/076149 dated Jan. 22, 2019.

* cited by examiner

METHOD FOR SETTING A MEDICAL IMAGING PROTOCOL, SYSTEM FOR SETTING A MEDICAL INSTRUMENT, COMPUTER PROGRAM AND COMPUTER-READABLE MEDIUM

PRIORITY STATEMENT

This application is the national phase under 35 U.S.C. § 371 of PCT International Application No. PCT/EP2018/076149 which has an International filing date of Sep. 26, 2018, which designated the United States of America and which claims priority to European patent application no. EP 17194984.5 filed Oct. 5, 2017, the entire contents of each of which are hereby incorporated herein by reference.

FIELD

Embodiments of the present invention generally relate to a method for setting a medical imaging protocol, a system for setting a medical instrument, a computer program product and a computer-readable medium.

BACKGROUND

Medical imaging protocols define a type of modality for recording a medical imaging data set, i.e. the medical imaging device such as a CT (computer tomography)-scanner, a MRT (magnetic resonance tomography)-scanner or a US (ultrasound)-scanner and a set of configuration and/or reconstruction parameters that are chosen for recording and visualising the medical imaging data set. Usually the medical imaging protocol is adapted to the patient, for example to a size of the patient or to a sex of the patient. Thereby, the medical imaging protocol is selected by a clinician based on his experience. In particular, the clinician usually suggests a familiar configuration and/or reconstruction parameter set for getting a visualized medical imaging data set having a good overall quality.

SUMMARY

The inventors have discovered that, as a consequence, the visualized medical image data set might not be optimized to parts that are relevant for an individual analysis of the visualized medical imaging data set, especially in view of confirming a specific provisional diagnostic finding. Further, they have discovered that, a suboptimal choice of an imaging procedure may inherently yield inadequate probability values for confirming or excluding a provisional diagnostic finding, while poor medical imaging protocols may render the imaging procedure inconclusive. This directly impacts costs and quality of confirming a diagnostic finding and may impact the overall quality for a given episode of care.

At least one embodiment of the present invention provides a method for providing a medical imaging protocol that further supports a clinician for confirming his provisional diagnostic findings.

Embodiments are directed to a method for setting a medical imaging protocol, a system, a computer program product and a computer readable computer medium.

According to a first embodiment of the present invention, a method for setting a medical imaging protocol is provided, comprising:

providing an information data set assigned to a patient, wherein the information data set includes an information about a provisional diagnostic finding regarding the patient;

assigning a probability value for a positive finding of the provisional diagnostic finding to the information data set; and automatically providing the medical imaging protocol, wherein the medical imaging protocol is adapted to the provisional diagnostic finding such that an analysis of a result of the medical imaging protocol changes the probability value.

According to another embodiment of the present invention a system for configuring a medical instrument comprising the medical instrument and a server is provided, wherein the system is configured for:

providing an information data set assigned to a patient, wherein the information data set includes an information about a provisional diagnostic finding regarding the patient;

assigning a probability value for a positive finding of the provisional diagnostic finding to the information data set; and automatically setting the medical imaging protocol, wherein the medical imaging protocol is adapted to the provisional diagnostic finding such that an analysis of an outcome being result of the medical imaging protocol changes the probability value.

Preferably the system comprises a control unit being configured for at least:

assigning a probability value for a positive finding of the provisional diagnostic finding to the information data set; and/or automatically providing the medical imaging protocol, wherein the medical imaging protocol is adapted to the provisional diagnostic finding such that an analysis of an outcome being result of the medical imaging protocol changes the probability value. Preferably the system comprising a control unit that has a processor being configured for executing at least one of the steps described above.

Another embodiment of the present invention is directed to a computer program product for carrying out the steps of the method according to an embodiment of the present invention when the computer program product is loaded into a memory of a programmable device.

A further embodiment of the present invention is directed to a computer-readable medium on which is stored a program elements that can be read and executed by a computer unit in order to perform steps of the method according to an embodiment of the present invention when the program elements are executed.

Another embodiment of the present invention is a computer program product for carrying out the steps of the method according to an embodiment of the present invention when the computer program product is loaded into a memory of a programmable device.

A further embodiment of the present invention is a computer-readable medium on which is stored a program elements that can be read and executed by a computer unit in order to perform steps of the method according to an embodiment of the present invention when the program elements are executed by the computer unit.

DETAILED DESCRIPTION OF THE EXAMPLE EMBODIMENTS

Figure 1:
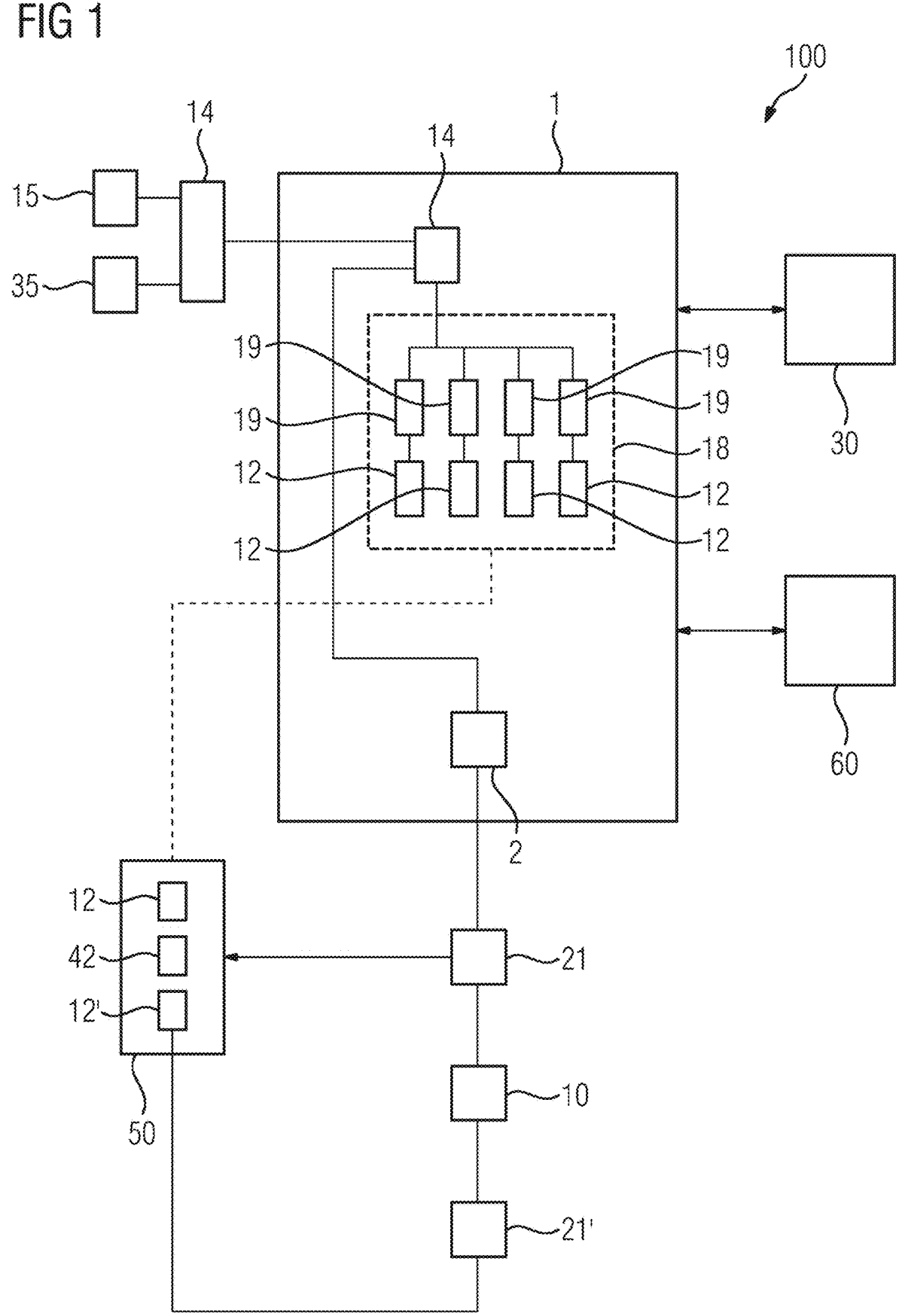
FIG. 1 shows a block diagram illustrating a system for setting a medical image data set according to a preferred embodiment of the present invention.

According to a first embodiment of the present invention, a method for setting a medical imaging protocol is provided, comprising:

providing an information data set assigned to a patient, wherein the information data set includes an information about a provisional diagnostic finding regarding the patient;

assigning a probability value for a positive finding of the provisional diagnostic finding to the information data set; and automatically providing the medical imaging protocol, wherein the medical imaging protocol is adapted to the provisional diagnostic finding such that an analysis of a result of the medical imaging protocol changes the probability value.

In contrast to the state of the art, the medical imaging protocol of at least one embodiment is individualized by focussing or concentrate the recording of a medical imaging data set to relevant parts in order to change the probability value of the provisional diagnostic finding. In particular, the medical imaging protocol of at least one embodiment is adapted such that the output or result of the medical imaging protocol, i.e. the medical image data set, is focussed to relevant issues for confirming or excluding the provisional diagnostic finding.

For example, the result of the medical imaging protocol of at least one embodiment is a visualisation of the medical imaging data set and the visualisation is optimized to those parts being relevant for the provisional diagnostic finding, in particular for a rule-in- or a rule-out-decision regarding the provisional diagnostic finding. Preferably, for a final diagnostic finding several exams have to be performed, in particular several medical imaging protocols, and after each of the exams the probability value increases after executing the medical imaging protocol.

In particular, in at least one embodiment it is provided that after each executed medical imaging protocol a further medical imaging protocol is adapted. Further, a control unit is preferably provided, wherein the control unit has a processor being configured at least for:

automatically setting the medical imaging protocol, wherein the medical imaging protocol is adapted to the provisional diagnostic finding such that an analysis of a result of the medical imaging protocol changes the probability value.

The term "information data set" preferably comprises a set of information needed for providing the probability value and/or setting the medical imaging protocol. In particular, the provisional diagnostic findings comprises symptoms of the patient and/or an expected disease, i.e. suspected condition of the patient. It is also thinkable that the symptoms are provided to the control unit and the control unit suggests one or several potential provisional diagnostic findings based on the symptoms of the patient. It is also thinkable that a preliminary probability value is incorporated into the information data set. Thereby the preliminary probability value is entered via an input device or a human machine interface and/or a prevalence mapper is used to infer the preliminary probability based on a general or adjusted prevalence of a disease from literature, for example from an existent statistic. For example the respective preliminary probability values for a patient complaining about acute chest pain for AAA (abdominal aortic aneurysm), PE (pulmonary embolism) and lung disease is estimated based on various scores (such as a SYNTAX score for grading a coronary anatomy of the patient) and set to 5% (for AAA), 5% (for PE) and 90% (for a ling disease).

The term "probability value" describes a probability for confirming the provisional diagnostic. In particular, the probability value for identifying an image finding in the recorded medical imaging data set. Preferably, the probability value is provided or calculated by the control unit.

The term "medical imaging protocol" preferably describes a set of configuration and/or reconstruction parameters for executing a medical imaging process. The medical imaging protocol for example comprises a choices for a modality, such for using a x-ray-scanner, a CT (computer tomography)-scanner, MRT (magnetic resonance tomography)-scanner, a ultrasound-scanner, a SPECT (single photon emission computed tomography)-scanner as well as the body region of the patient such as chest, head or abdomen. Furthermore, the medical imaging protocol comprises information about the contrast and the native format as well as parameters for recording and reconstructing the medical image data set, such as a dose, a contrast, a resolution, a gating, a mapping, a sequence, a field of view, a gradient parameter, a Doppler parameter and/or reconstruction parameters.

Particularly advantageous embodiments and features of the invention are given by the claims as revealed in the following description. Features of different claim categories may be combined as appropriate to give further embodiments not described herein.

According to a preferred embodiment of the present invention the medical imaging protocol is executed. Preferably, the medical imaging device is in communication with the control unit and the medical imaging protocol, in particular the configuration parameters and/or the reconstruction parameters are transferred to the medical imaging device and the medical imaging device adopts the configuration parameters and/or reconstruction parameters, in particular automatically.

In another preferred embodiment it is provided that a list comprising potential imaging findings is provided, wherein to each potential imaging findings a probability value is assigned. Preferably, the potential imaging findings depends on the information data set, for example the provisional diagnostic finding. In particular, it is provided that a list of potential imaging findings based on the information data set is provided, wherein to each of the potential imaging findings a probability value is selected.

In particular, the probability value define for each imaging finding a probability for confirming a disease. Thus, it is possible to concentrate the medical imaging protocol to the potential imagine finding having the highest probability. Preferably, a list of potential imaging findings and the corresponding medical imaging protocols are monitored to a clinician and/or the clinician selects one of the medical imaging protocols suggested to the list of potential imaging findings. In particular, the list of imaging findings is based on a radiological encyclopedia and/or a terminology knowledge base, such as GAMUTS, STATDX and/or RADLEX.

It is also thinkable that the probability value can be initially determined from existent radiological knowledge-base, publications or is initialized by experts. For example, the probability value is based on a likehood ration calculations and/or Fagan namograms. Furthermore, it is conceivable that a probability value is presented for ruling out a disease in an equivalent manner. Preferably, for each imaging finding having a probability value greater than a threshold value a list of configuration parameters and/or reconstruction parameter is provided, in particular a list of configuration parameters and/or reconstruction parameter that maximizes the probability value. For example, the probability values are based on bench experiments using phantoms or by using respective images.

Preferably, the information data set is based on a patient related data base and/or is created by an input device. In particular the control unit is in communication with the patient related data base. Thus, the information data set can automatically be complemented by adding additional information. For example, a patient complains about acute chest pain and a emergency physician puts in a CT in order to rule out AAA (abdominal aortic aneurysm) and PE (pulmonary embolism). By accessing a patient related data base the control unit is further informed about a lung nodules documented during a previous exam. The input device is preferably a human machine interface such as a keyboard or a touchscreen.

According to a preferred embodiment of the present invention, it is provided that a trained artificial network is used for providing the medical imaging protocol. In particular, the configuration parameters and/or reconstruction parameters are optimized by using a trained artificial network.

In particular, it is provided that a further probability value is provided after executing the medical imaging protocol. This further probability value can be used for training the artificial network advantageously, for example by using a machine learning (ML) mechanism or in particular a deep learning mechanism. The machine learning mechanism further uses retrospective radiological and clinical reports for training, for example. Preferably, the further probability value is provided by a clinician by entering the further probability to the control unit. Alternatively it is also thinkable that control unit analyses the medical imaging device and automatically provides the further probability value.

In particular, the medical imaging protocol comprises a type of modality and/or a configuration parameter for configuring a medical imaging device and/or for reconstructing a medical imagine data set of the medical imaging device. Preferably, the medical imaging protocol defines both the type of medical imaging device to use on the one hand and the configuration parameter and/or reconstruction parameters on the other hand.

In another embodiment of the present invention, it is provided that the probability value, the further probability value and/or the medical imaging protocol are provided to a user via a screen and/or an output device. Thus, a clinician is informed about the probability value, the further probability and/or the medical imaging protocol.

Preferably, it is provided that the information data set comprises:
 an initial assessment
 constraints for imaging and/or
 a result of previous examination. Further information from the EMR (ErfahrungsMedizinschesRegister) and PACS (Picture Archiving and Communication System) can be used to infer suspected conditions and diagnoses.

It is also conceivable that a mapper module, in particular a ICD (international Statistical Classification of Diseases and Related Health Problems)-mapper is used to map or encode an entered information data set to an ICD-confirm list. It is also thinkable that the information data set has information about imaging constraints, in particular patient specific imaging constraints such as allergies to contrast agents, phase markers or the like. It is also thinkable that the information about imaging constrains is correlated to an information of the EMR. For example, due to acute chest pain a patient suffers from shortness of breath and will not be able to follow breathing commands.

In another embodiment of the present invention, it is provided that the probability value and/or the further probability value are assigned by using a further artificial network. Thus, the probability value, in particular the probability value for a imaging finding, can be further optimized by learning the probability using retrospective radiological and clinical reports and applying conventional machine learning mechanism and/or deep learning mechanism. It is also thinkable to use the further artificial network to analyse the recorded medical imaging data sets for providing the further probability value.

Preferably, the medical imaging protocol comprises an information about the body region, a contrast information, a coding information and/or a billing information. In particular a medical imaging protocol includes a type of modality, a short description, a body region, a contrast as well as coding and billing information, preferably specified to a region and/or country. This includes information such as CPT (Current Procedural Terminology), ICD or HSPTC (Healthcare Common Procedure Coding System) coding. For example, the medical imaging protocol comprises the following information: CT thorax, w/o contrast, followed by contrast, CPT 71270.

According to a further embodiment of the present invention, it is provided that at least one step is performed at a server or system of server. For example, at least one step is performed by using a cloud or a network. It is also thinkable that the information data set is transferred to the server or the system of server and subsequently the medical imaging protocol is provided by the server or the system of server, i.e. the control unit is located at the server side. Alternatively, it is thinkable that the control unit is incorporated into a workstation, such as a personal computer, and the control unit access the server or system of server on demand.

According to another embodiment of the present invention a system for configuring a medical instrument comprising the medical instrument and a server is provided, wherein the system is configured for:
 providing an information data set assigned to a patient, wherein the information data set includes an information about a provisional diagnostic finding regarding the patient;
 assigning a probability value for a positive finding of the provisional diagnostic finding to the information data set; and
 automatically setting the medical imaging protocol, wherein the medical imaging protocol is adapted to the provisional diagnostic finding such that an analysis of an outcome being result of the medical imaging protocol changes the probability value.

Preferably the system comprises a control unit being configured for at least:
 assigning a probability value for a positive finding of the provisional diagnostic finding to the information data set; and/or
 automatically providing the medical imaging protocol, wherein the medical imaging protocol is adapted to the provisional diagnostic finding such that an analysis of an outcome being result of the medical imaging protocol changes the probability value. Preferably the system comprising a control unit that has a processor being configured for executing at least one of the steps described above.

Another embodiment of the present invention is directed to a computer program product for carrying out the steps of the method according to an embodiment of the present invention when the computer program product is loaded into a memory of a programmable device.

A further embodiment of the present invention is directed to a computer-readable medium on which is stored a program elements that can be read and executed by a computer unit in order to perform steps of the method according to an embodiment of the present invention when the program elements are executed.

Another embodiment of the present invention is a computer program product for carrying out the steps of the method according to an embodiment of the present invention when the computer program product is loaded into a memory of a programmable device.

A further embodiment of the present invention is a computer-readable medium on which is stored a program elements that can be read and executed by a computer unit in order to perform steps of the method according to an embodiment of the present invention when the program elements are executed by the computer unit.

Preferably, the programmable device and/or the computer unit are incorporated into the system for analysing the medical imaging data set described above, in particular into the control unit.

In FIG. 1 a block diagram illustrating a system for setting a medical imaging protocol 42 according to a preferred embodiment of the present invention is shown. In general, the medical imaging protocol 42 defines a strategy for recording a medical image data set of a patient. This includes for example choosing the proper type of modality, i.e. the proper type of medical imaging devices 10, as well as setting the proper configuration parameters of the medical imaging device 10 for recording the medical imaging data set and/or reconstructing the medical imaging data set for visualisation.

In order to optimize a workflow for getting a final diagnostic finding it is provided that the medical imaging protocol 42 is adapted. Preferably, the medical imaging protocol 42 is adapted after a first assessment or a first exam of the patient or after each exam, when several exams have to be preformed for getting the final diagnostic finding. In particular, it is provided that the medical imaging protocol 42 is adapted based on an information data set 14, wherein the information data set 14 includes an information about a provisional diagnostic finding, for example a first assessment of a state of the patient or the assessment after a previous exam.

For adapting the medical imaging protocol 42 a control unit 1 is provided, wherein the control unit 1 might be incorporated into a workstation, such as a personal computer, and/or a server 60 and further comprises a processor configured for providing a medical imaging protocol 42. In particular, it is provided that in the beginning a probability value 12 is set based on the provisional diagnostic findings by the control unit 1. The probability value 12 represents the chance for confirming the provisional diagnostic finding.

In particular, it is provided that the medical imaging protocol 42 is adapted to the provisional diagnostic finding such that an analysis of a result of the medical imaging protocol changes 42 the probability value 12 or the medical imaging protocol 42 is adapted such that the recorded medical image data set is focussed on relevant issues for the provisional diagnostic finding. Preferably, the medical imaging protocol 42 suggests a specific configuration for setting the medical imaging device 10 and/or for reconstructing a medical imaging data set being recorded with the medical imaging device 10, wherein the configuration is adapted such that it is specialized to the provisional diagnostic finding. Thus, it is possible to focus the medical imaging protocol for confirming or for excluding the provisional diagnostic finding. In particular, a trained artificial network 30 is used for providing the probability value 12 and/or the medical imaging protocol 42. In particular, the medical imaging protocol 42 comprises a configuration that [under comparable conditions, i.e. a comparable information data set 14, resulted in a largest change of the probability value in the past].

Preferably, the information data set 14 is at least partially based on a patient related data base 35 and/or is created by an input device 15. For instance, the information data set 14 comprises:
an initial assessment
constraints for imaging and/or
a result of previous examination.

In particular, the control unit 2 has access to the patient related data base 35 for feeding information into the information data set 14. Alternatively, the information data set 14 is at least partially entered via the input device 15, i.e. a human machine interface. It is preferably provided that control unit 1 is configured such that a list 19 comprising potential image findings 18 is realized, wherein to each potential image finding 18 a probability value 12 is assigned. Thus, the clinician is informed about different potential image findings 18 correlated to the current provisional diagnostic finding.

By comparing the probability values 12 of the different potential image finding 19, it is possible to select the medical imaging protocol having the highest probability for confirming or excluding the provisional diagnostic finding. It is also considerable that the provisional diagnostic finding includes symptoms of the patient and the control unit 1 suggests the list of provisional diagnostic findings and/or potential image findings based on the symptoms. By selecting one of the several potential image findings 19, the medical imaging protocol 42 is adapted to the selected potential provisional finding. It is also thinkable that medical imaging protocols 42 are provided for each of the potential image findings 19 having a probability value 12 bigger than a threshold value. Preferably the medical imaging protocol is transferred to an output device 21, such as a workstation and/or to the medical imaging device 10, and/or a screen 50.

Furthermore, after executing the medical imaging protocol 42 a further probability value 12' is provided, for example by adding the further probability 12' to the control unit 1 by a clinician, for example by using the input device 15, or by analysing the medical imaging data set by the control unit 1. Thus, the information about the further probability 12' can be used for training the artificial neuronal network 30 and/or for renewing or adapting the medical imaging protocol 42 for the subsequent proceedings. In particular, the control unit 1 takes into account previous medical imaging protocols 42 for configuring the next medical imaging protocol 42 in a chain of exams.

In particular, it is provided that the probability value 12, the further probability value 12' and/or the medical imaging protocol 42 are presented on a display or screen, for example a screen of a workstation, a tablet and/or a smartphone. Thus, the clinician is informed about the probability value 12, the further probability value 12' and/or the medical imaging protocol 42 and the clinician can configure the selected medical imaging device 10 according to the medical imaging protocol 42 for executing the medical imaging protocol 42. It is also thinkable that the control unit 1 is in communication with the medical imaging device 10 and configuration and/or reconstruction parameters of the medical imaging device are set automatically by the control unit 1. It is also thinkable that medical imaging protocol, for example presented on the screen, comprises an information about the body region, a contrast information, a coding information and/or a billing information.

Figure 2:
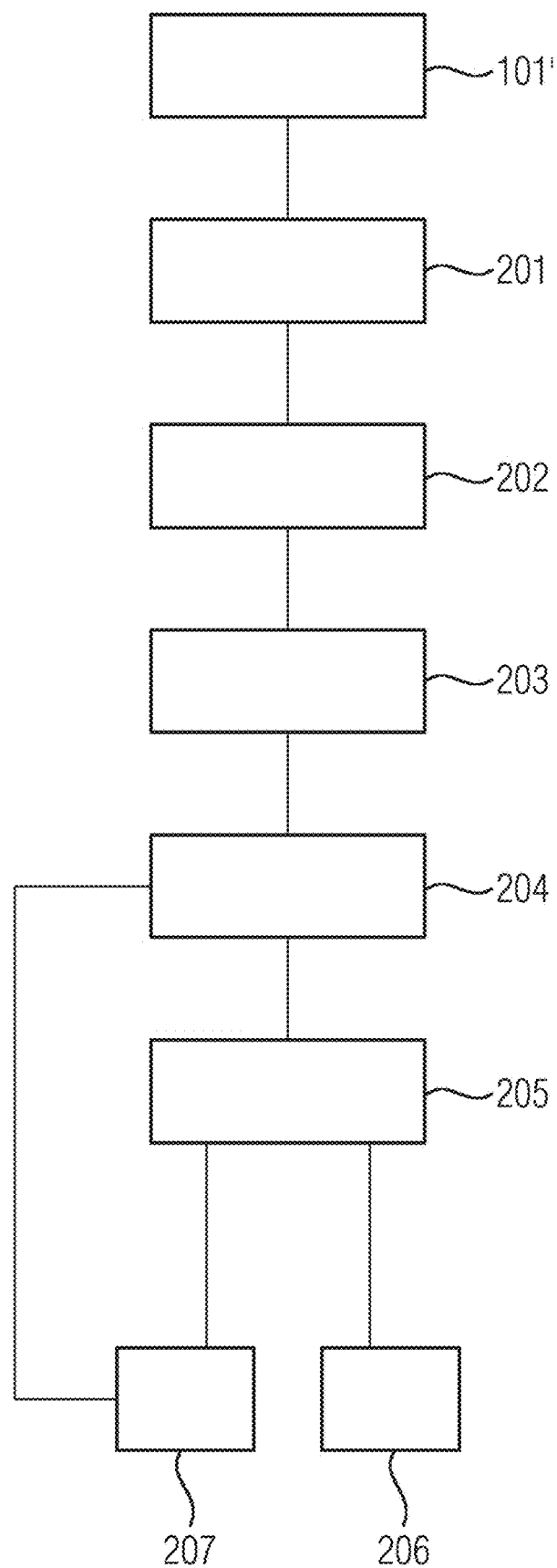
FIG. 2 shows a flow diagram illustrating the method for setting the medical imaging protocol according to a preferred embodiment of the present invention.

In FIG. 2 a flow diagram illustrating the method for setting the medical imaging protocol according to a preferred embodiment of the present invention is illustrated. In particular the FIG. 2 presents a method comprising:

providing 101' an information data set 14, providing 201 a potential image finding 19 related to the information data set 14, in particular a list 18 of several potential image findings 19, assigning 202 a probability value to the information data set 14, in particular to the potential image finding or to each potential image finding, automatically providing 203 the medical imaging protocol 42, wherein the medical imaging protocol 42 is adapted to the provisional diagnostic finding such that an analysis of a result of the medical imaging protocol changes the probability value 12, in particular by using a artificial network, executing 204 the medical imaging protocol 42 providing 205 a further probability after executing the medical image protocol, using the medical image protocol, the information data set, the probability value and the further probability value for training 206 the artificial network presenting 207 the medical image protocol, the probability value and the further probability on a screen.

The invention claimed is:

1. A method for setting a medical imaging protocol via a controller, comprising:
providing an information data set assigned to a patient, the information data set including information about a provisional diagnostic finding regarding the patient;
assigning a first probability value for a positive finding of the provisional diagnostic finding to the information data set provided; and
automatically setting the medical imaging protocol, the medical imaging protocol being adapted to the provisional diagnostic finding such that an analysis of a result of the medical imaging protocol changes the first probability value assigned,
wherein the medical imaging protocol includes a configuration parameter for at least one of configuring a medical imaging device and reconstructing a medical imaging data set of the medical imaging device.

2. The method of claim 1, comprising:
executing the medical imaging protocol.

3. The method of claim 2, wherein a list including potential imaging findings is provided for selecting one medical imaging protocol, wherein a second probability value is assigned to each of potential image finding of the potential image findings.

4. The method of claim 2, wherein the information data set is at least one of based on a patient related data base and created via an input device.

5. The method of claim 2, wherein a trained artificial neural network is used for providing the medical imaging protocol.

6. A non-transitory computer-readable medium, storing program elements, readable and executable by a computer unit, to perform the method of claim 2 when the program elements are executed by the computer unit.

7. The method of claim 1, wherein a list including potential imaging findings is provided for selecting one medical imaging protocol, wherein a second probability value is assigned to each of potential image finding of the potential image findings.

8. The method of claim 1, wherein the information data set is at least one of based on a patient related data base and created via an input device.

9. The method of claim 1, wherein a trained artificial neural network is used for providing the medical imaging protocol.

10. The method of claim 1, wherein a further probability value is provided after the automatically setting of the medical imaging protocol.

11. The method of claim 1, wherein the medical imaging protocol includes a type of modality for at least one of configuring the medical imaging device and reconstructing a medical imaging data set of the medical imaging device.

12. The method of claim 1, wherein at least one of the first probability value, a further probability value and the medical imaging protocol are provided to a user via at least one of a screen and an output device.

13. The method of claim 1, wherein the information data set includes at least one of:
an initial assessment,
constraints for imaging, and
a result of previous examination.

14. The method of claim 1, wherein at least one of the first probability value and a further probability value are assigned by using a further artificial neural network.

15. The method of claim 1, wherein the medical imaging protocol includes at least one of an information about a body region, a contrast information, a coding information and a billing information.

16. The method of claim 1, wherein at least a portion of the method is performed at a server or system of server.

17. A non-transitory computer program product, storing program elements for carrying out the method of claim 1 when the computer program product is loaded into a memory of a programmable device and the program elements are executed.

18. A non-transitory computer-readable medium, storing program elements, readable and executable by a computer unit, to perform the method of claim 1 when the program elements are executed by the computer unit.

19. The method of claim 1, wherein the medical imaging protocol suggests a specific configuration for at least one of setting the medical imaging device and reconstructing the medical imaging data set, being recorded with the medical imaging device, and wherein the specific configuration is adapted to be specialized to the provisional diagnostic finding.

20. A system for setting a medical instrument with a medical imaging protocol, the system being configured to
provide an information data set assigned to a patient, the information data set including information about a provisional diagnostic finding regarding the patient;
assign a first probability value for a positive finding of the provisional diagnostic finding to the information data set provided; and
automatically set the medical imaging protocol, the medical imaging protocol being adapted to the provisional diagnostic finding such that an analysis of an outcome being result of the medical imaging protocol changes the first probability value assigned,
wherein the medical imaging protocol includes a configuration parameter for at least one of configuring a medical imaging device and reconstructing a medical imaging data set of the medical imaging device.

* * * * *